United States Patent [19]

Noske et al.

[11] Patent Number: 4,836,191

[45] Date of Patent: Jun. 6, 1989

[54] LITHOTRIPSY WORK STATION

[75] Inventors: Erich Noske, Weiher; Manfred Pfeiler, Erlangen; Helmut Reichenberger, Eickental, all of Fed. Rep. of Germany

[73] Assignee: Siemens Aktiengesellschaft, Berlin and Munich, Fed. Rep. of Germany

[21] Appl. No.: 145,984

[22] Filed: Jan. 20, 1988

[30] Foreign Application Priority Data

Jan. 26, 1987 [DE] Fed. Rep. of Germany ... 8701218[U]

[51] Int. Cl.⁴ .............................................. A61B 17/22
[52] U.S. Cl. .................................... 128/24 A; 128/328
[58] Field of Search ..................... 128/24 A, 328, 660, 128/804

[56] References Cited

U.S. PATENT DOCUMENTS 4,669,483 6/1987 Hepp et al. ......................... 128/328
4,674,505 6/1987 Pauli et al. .......................... 128/328

FOREIGN PATENT DOCUMENTS

| 528152 | 4/1983 | Australia . | |
| 0131654 | 1/1985 | European Pat. Off. | 128/328 |
| 0225104 | 6/1987 | European Pat. Off. | 128/24 A |
| 170238 | 7/1951 | Fed. Rep. of Germany | 128/24 A |
| 3532678 | 3/1987 | Fed. Rep. of Germany | 128/24 A |
| 1514314 | 2/1968 | France | 128/24 A |
| 1115721 | 9/1984 | U.S.S.R. | 128/328 |

Primary Examiner—Ruth S. Smith
Attorney, Agent, or Firm—Hill, Van Santen, Steadman & Simpson

[57] ABSTRACT

A lithotripsy work station which has a plurality of shockwave generators which are adjustably mounted on a curved rail which, in turn, is mounted for pivotal movement in all directions relative to a fixed frame of the work station. Thus, a calculi can be sound-irradiated with shockwaves from any possible angle, as required by respective clinical situation.

5 Claims, 1 Drawing Sheet

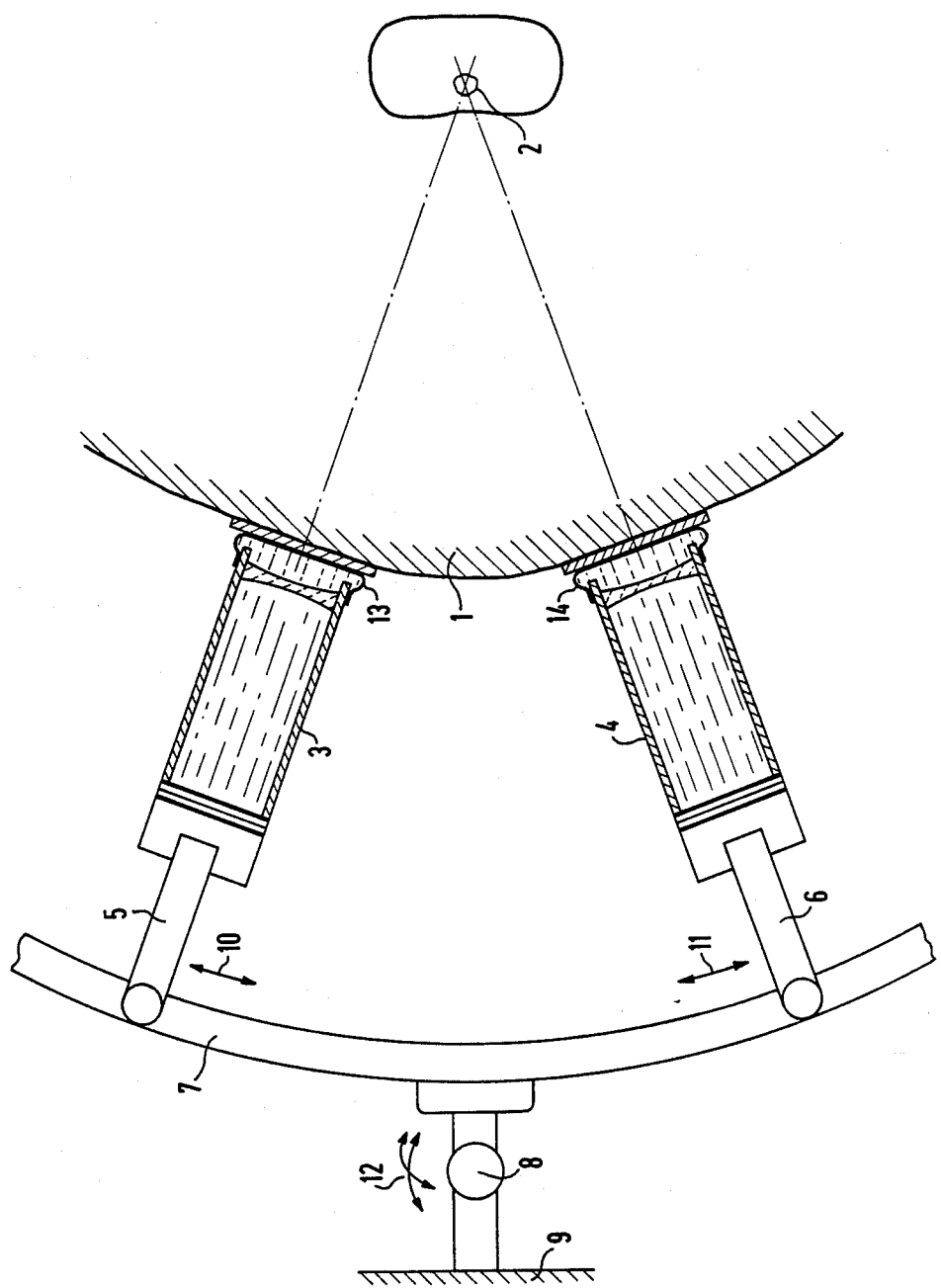

LITHOTRIPSY WORK STATION

BACKGROUND OF THE INVENTION

The present invention is directed to a lithotripsy work station comprising a plurality of shockwave generators which are adjustably mounted on a mounting arrangement, so that they can be simultaneously applied to a patient.

A lithotripsy work station is known wherein the shockwave generators are mounted under the patient support so that, respectively, one of these can be swiveled from a parking or retracted position into a working position, depending upon which side of the patient the shockwaves are to enter. The angle at which the shockwave generator is arranged on a common holder is fixed.

SUMMARY OF THE INVENTION

The object of the present invention is to provide a lithotripsy work station having more than one shockwave generator wherein the direction and angle at which a radiation of the calculi or stone with the shockwaves can be varied and adapted to the respective clinical situation as desired. This object is inventively achieved in an improvement in a lithotripsy work station having a plurality of shockwave generators, means for adjustably mounting the shockwave generators relative to the patient. The improvements are that the means for mounting is constructed so that the irradiation angle is individually adjusted for each shockwave generator.

Given the lithotripsy work station of the present invention, every shockwave generator can be individually set within a large range relative to the calculi to be respectively sound-irradiated so that the respective clinical situation can be optimally taken into consideration. It is, therefore, possible to mount two or more shockwave generators individually on a single holder. The shockwave generators can be of different types, for example, they can be either electro-magnetic or piezo ceramic types. During operation, every shockwave generator can be individually applied to the body of the patient via contact means, for example, via a membrane inflatable with a hydrostatic pressure or coupling material.

A practical structural solution is that the holder comprises an approximately circular curved guide or track for the shockwave generators and that this holder is mounted by means which allow swiveling or pivoting in all directions around a single point by utilizing a ball-and-socket joint. An especially versatile adjustment of every individual shockwave generator in space is possible with this embodiment.

Other advantages and features will be readily apparent from the following description of the preferred embodiment, the drawing and claims.

BRIEF DESCRIPTION OF THE DRAWING

The FIGURE is a side view, with portions broken away for purposes of illustration, of the apparatus in accordance with the present invention.

DESCRIPTION OF THE PREFERRED EMBODIMENT

The drawing shows a patient 1 who, in the example, has a kidney with a kidney stone or calculi 2. The kidney stone 2 is to be disintegrated by a sound-irradiation with shockwaves proceeding from two shockwave generators 3 and 4. The shockwave generators 3 and 4 are constructed in a known manner, such as disclosed by U.S. Pat. No. 4,674,505, whose disclosure is incorporated by reference and which patent claims priority from German Patent Application No. 33 28 051.

Every shockwave generator 3 and 4 is mounted for longitudinal displacement on its axis, for example, with the generator 3 being mounted for displacement on an arm 5 while the generator 4 is mounted for displacement on an arm 6. Each of the arms 5 and 6 are mounted for movement along a circularly curved rail 7. The rail 7 is connected to a rigid frame 9 of the apparatus by a ball-and-socket joint 8. Thus, the shockwave generators 3 and 4 are adjustable relative to the rail in the direction of the double arrows 10 and 11, respectively, and the units 3, 4 and a rail 7 can be adjusted in space in the direction of arrows 12 so that the whole arrangement of the two shockwave generators 3 and 4 and rail 7 can pivot in all directions around a point formed by the ball-and-socket joint 8. It is noted that the mounting means includes an arrangement for locking each of the arms 5 and 6 in the desired position on the rail 7 and for locking the ball-and-socket joint 8 in any of the desired pivot positions.

The shockwave generators 3 and 4, with which the kidney stone 2 is to be irradiated, are positioned so that they engage the surface of the patient 1 with the assistance of hydraulically inflated membranes 13 and 14, which are illustrated as being filled with a coupling fluid. Depended on the clinical situation, the shockwaves 3 and 4 can be operated or triggered together, individually or in any desired sequence.

Although various minor modifications may be suggested by those versed in the art, it should be understood that we wish to embody within the scope of the patent granted hereon all such modifications as reasonably and properly come within the scope of our contribution to the art.

We claim:

1. A lithotripsy work station comprising a frame, a plurality of shockwave generators for irradiating a patient with shockwaves, and common mounting means for adjustably positioning said plurality of shockwave generators relative to said frame, said mounting means being constructed so that the shockwave generators of said plurality of shockwave generators are adjustable to simultaneously engage the patient for irradiating the patient with shockwaves under respective different irradiation angles, and said mounting means being further constructed so that said respective irradiation angles are individually adjustable for each shockwave generator of said plurality of shockwave generators in a common plane.

2. A lithotripsy work station according to claim 1, wherein the mounting means comprises a curved guide, said shockwave generators of said plurality of shockwave generators being adjustably mounted to move along a curved path on said curved guide.

3. A lithotripsy work station according to claim 2, wherein the mounting means includes a ball and socket joint between the guide and frame so that the guide is mounted on the frame for pivotal movement in all directions by said ball and socket joint.

4. A lithotripsy work station comprising a frame, a plurality of shockwave generators for irradiating a patient with shockwaves, and mounting means for adjustably positioning said plurality of shockwave generators on said frame to simultaneously engage a patient for irradiating a patient with shockwaves under different radiation angles, said mounting means including a curved rail having a curved path and being pivotably mounted on said frame and an arm for each of said shockwave generators adjustably mounted on said rail and movable along said curved path to change the angle of each generator relative to the other generators in a common plane defined by the rail and said arms.

5. A lithotripsy work station according to claim 4, wherein the rail is pivotably mounted on the frame by a ball and socket joint.

* * * * *